United States Patent [19]

Porcelli et al.

[11] 4,252,741

[45] Feb. 24, 1981

[54] CARBONYLATION WITH GROUP VIII NOBLE METAL CATALYSTS

[75] Inventors: Richard V. Porcelli, Yonkers; Vijay S. Bhise; Arnold J. Shapiro, both of New York, all of N.Y.

[73] Assignee: Halcon Research & Development Corp., New York, N.Y.

[21] Appl. No.: 949,344

[22] Filed: Oct. 6, 1978

[51] Int. Cl.³ ............................................. C07C 51/56
[52] U.S. Cl. .................................. 260/549; 560/232; 560/233; 568/484
[58] Field of Search ......... 260/549, 604 HF, 604 AC; 560/232, 233

[56] References Cited

U.S. PATENT DOCUMENTS 4,002,677  1/1977  Magheri et al. ..................... 260/549

4,115,444  9/1978  Rizkalla ................................ 260/549

*Primary Examiner*—Paul J. Killos
*Attorney, Agent, or Firm*—William C. Long; David Dick; Riggs T. Stewart

[57] ABSTRACT

In the carbonylation of alkyl esters in the presence of a Group VIII noble metal catalyst to produce a reaction mixture comprising volatile components and the non-volatile Group VIII noble metal catalyst, and the volatile components are separated from the catalyst, catalyst activity is maintained by providing a partial pressure of hydrogen of at least 10 psi during the separation of the volatile products. A partial pressure of at least 15 psi of carbon monoxide is also preferably provided, particularly when a metal promoter for the Group VIII noble metal catalyst is present, during such separation.

5 Claims, No Drawings

CARBONYLATION WITH GROUP VIII NOBLE METAL CATALYSTS

This invention relates to the preparation of anhydrides of carboxylic acid, more particularly mono-carboxylic acids, and especially the anhydrides of lower alkalnoic acids, such as acetic anhydride, by carbonylation.

Acetic anhydride has been known as an industrial chemical for many years and large amounts are used in the manufacture of cellulose acetate. It has commonly been produced on an industrial scale by the reaction of ketene and acetic acid. It is also known that acetic anhydride can be produced by the decomposition of ethylidene diacetate, as well as by the oxidation of acetaldehyde, for example. Each of these "classic" processes has well-known drawbacks and disadvantages and the search for an improved process for the production of acetic anhydride has been a continuing one. Proposals for producing anhydrides by the reaction of carbon monoxide upon various reactants (carbonylation) have been described, for example, in Reppe et al. U.S. Pat. Nos. 2,729,561, 2,730,546 and 2,789,137, using cobalt or nickel catalysts under very high pressure. More recently, carbonylation at low pressures has been proposed in processes employing Group VIII noble metal catalysts with and without promoters. Processes of this type are disclosed in Lapporte et al. U.S. Pat. No. 3,927,078 and in Kuckertz U.S. Pat. No. 4,046,807. Particularly attractive processes for preparing carboxylic acid anhydrides, including acetic anhydride, by the carbonylation of methyl acetate are disclosed in British Pat. No. 1,468,940 which is based on co-pending U.S. applications of Colin Hewlett Ser. No. 394,220, filed Sept. 4, 1973 and Ser. No. 467,977, filed May 8, 1974, and in U.S. Pat. No. 4,115,444 of Sept. 19, 1978. Belgian Pat. No. 839,321 which is the counter-part of U.S. application Ser. No. 654,662 filed Feb. 5, 1976, discloses a process for the carbonylation of methyl acetate wherein the carbonylation is carried out in the presence of substantial amounts of hydrogen so that the acetic anhydride formed is accompanied by ethylidene diacetate, acetaldehyde and acetic acid. The disclosures of said British and Belgian patents, and said U.S. Pat. No. 4,115,444 are incorporated herein by reference.

Such carbonylations are carried out in the presence of Group VIII noble metals, i.e., rhodium, iridium, platinum, palladium, osmium and ruthenium, and their compounds, and in the presence of an iodide, with or without inorganic and/or organic promoters.

In carrying out such processes as described in these disclosures on a continuous basis, wherein volatile components of the carbonylation mixture are continuously separated from the relatively non-volatile Group VIII noble metal catalyst, and the catalyst reused for further carbonylation, it has been discovered that the Group VIII noble metal catalyst gradually loses its activity and, after prolonged use, may become essentially inactive from a practical standpoint. It is, of course, possible to replace the catalyst at this point but this is an expensive operation even if the deactivated catalyst can be reclaimed.

Processes for regenerating Group VIII noble metal catalysts are known. For exaple, Knifton U.S. Pat. No. 4,038,208 proposes to regenerate certain palladium catalysts by means of treatment with hydrogen peroxide and Knifton U.S. Pat. No. 4,048,093 uses organic peroxides for this purpose. BASF Dutch published Pat. No. application 77 03723 treats rhodium hydroformylation catalysts with oxygenated mineral acids and peroxides. Leach U.S. Pat. No. 4,007,130 treats rhodium and iridium catalysts with cation exchange resins. Japanese Pat. publication No. 73/43,799 in the name of Chisso Corp. reactivates rhodium catalysts by prolonged heating under a high-pressure atmosphere, e.g., for 14 hours under a pressure of about 68 atmospheres. Forster et al. U.S. Pat. No. 3,852,346 describes an olefin carbonylation process using a rhodium or iridium catalyst in which the carbonylation is carried out in the presence of a catalyst preserver or regenerator component which is hydrogen or a compound capable of forming hydrogen under reaction conditions.

In the case of the carbonylation of alkyl esters such as methyl acetate, however, it has been discovered that even when the carbonylation is carried out in the presence of hydrogen prior to separation of volatile components, catalyst deactivation nevertheless takes place.

It is, accordingly, an object of this invention to provide a process involving the carbonylation of alkyl esters such as methyl acetate to produce alkanoic anhydrides, such as acetic anhydride, wherein the activity of Group VIII noble metal catalysts is maintained even during prolonged continuous carbonylation operations.

In accordance with the invention, it has been discovered that this and other objects can be readily achieved by maintaining a partial pressure of hydrogen of at least 10 psi in the zone in which volatile components of the carbonylation mixture are continuously separated from the Group VIII noble metal. When the carbonylation is carried out in the presence of a metal promoter, such as chromium, it is also preferred to maintain a partial pressure of carbon monoxide of at least 15 psi in the separation zone.

Thus, in a typical case, carbonylation of an alkanoic ester such as methyl acetate is carried out continuously in the presence of a Group VIII noble metal, with or without the presence of a promoter, but in the presence of an iodide such as methyl iodide. Volatile components of the reaction mixture are then continuously separated from the relatively non-volatile Group VIII noble metal catalyst and the latter is continuously reused for further carbonylation. Typically, although not necessarily, the carbonylation takes place in a carbonylation zone and separation takes place by means of a flash distillation under a pressure lower than that prevailing in the carbonylation zone. Heat can be added or removed or the flash distillation can be carried out adiabatically, as will be apparent to persons skilled in the art. An adiabatic flash distillation employed in connection with the preparation of acetic acid is disclosed in Eubanks et al. U.S. Pat. No. 3,845,121. In accordance with the invention, during the separation of volatile components from the Group VIII noble metal catalyst, a hydrogen partial pressure of at least 10 psi is maintained and preferably, when a metal promoter such as a chromium promoter is present, there is also maintained a carbon monoxide partial pressure of at least 15 psi. It will be understood that while it is preferred to maintain the above specified minimum hydrogen and carbon monoxide partial pressure continuously during the separation, this is not essential and they may be intermittently maintained at or above these minima.

It has been surprisingly discovered that by maintaining a minimum hydrogen partial pressure of 10 psi during the separation step, the catalyst, even upon repeated reuse, maintains its original activity essentially indefinitely, whereas if no hydrogen partial pressure is maintained the catalyst loses its activity under repeated reuse and must eventually be replaced. In the case of the carbonylation of esters such as methyl acetate it has been surprisingly found that such deactivation occurs even when carbonylation is carried out as described in Forster et al. U.S. Pat. No. 3,852,346 but using an ester instead of an olefin as the carbonylation substrate.

It is believed that a fuller understanding of the invention will result from a discussion of representative carbonylation reactions with which the process of the invention will be typically associated.

Carbonylation involving an ester, such as methyl acetate, and carbon monoxide is typically carried out at temperatures of 20° C. to 500° C., preferably 100° to 300° C. under a carbon monoxide partial pressure of 0.1 to 15,000 psi, and, as mentioned, is facilitated by the use of a catalyst, most suitably a Group VIII noble metal, i.e., rhodium, iridium, ruthenium, palladium, osmium and/or platinum, as disclosed in Belgian Pat. Nos. 819,455 and 839,321, and in U.S. Pat. No. 4,115,444. For ease of description, the invention will be described in terms of the carbonylation of methyl acetate. It will, of course, be understood that methyl acetate can be replaced or supplemented with dimethyl ether in the feed. It has been observed that the dimethyl ether is converted to methyl acetate in the carbonylation reaction so that it may be considered a methyl acetate precursor. When, therefore, reference is made to methyl acetate as a feed to the carbonylation, it will be understood that the dimethyl ether precursor is also contemplated. As previously indicated, the invention is also fully applicable to the carbonylation of other alkyl esters of alkanoic acids such as those described in U.S. Pat. No. 4,115,444, British Pat. No. 1,468,940 and Belgian Pat. No. 819,455.

The Group VIII noble metal carbonylation catalyst can be supplied and used in any convenient form, viz, in the zero valent state or in any higher valent form. For example, the catalyst may be the metal itself in finely-divided form, or as a metal carbonate, oxide, hydroxide, bromide, iodide, chloride, lower alkoxide (methoxide), phenoxide or metal carboxylate wherein the carboxylate ion is derived from an alkanoic acid of 1 to 20 carbon atoms. Complexes of the metals can be employed, e.g. the metal carbonyls, such as iridium and rhodium carbonyls, e.g. hexarhodium hexadecacarbonyl, or as other complexes such as the carbonyl halides, e.g. iridium tri-carbonyl chloride $[Ir(CO)_3Gl]_2$ or chlorodicarbonyl rhodium dimer, or the acetylacetonates, e.g. rhodium acetylacetonate $Rh(C_5H_7O_2)_3$. It will be understood that the foregoing compounds and complexes and classes of compounds and complexes are merely illustrative of suitable forms of the Group VIII noble metal catalyst and are not intended to be limiting.

The metal employed may contain impurities normally associated with the commercially available metal or metal compounds, and need not be purified any further. Thus, the commercially available metal or metal compound is suitably employed.

The amount of Group VIII noble metal catalyst is in no way critical and is not a parameter of the process of the invention and can vary over a wide range. As is well known to persons skilled in the art, the amount of catalyst used is that which will provide the desired suitable and reasonable reaction rate since reaction rate is influenced by the amount of catalyst. However, essentially any amount of catalyst will facilitate the basic reaction and can be considered a catalytically-effective quantity. Typically, however, the catalyst is employed in the amount of 1 mol per 10 to 100,000 mols of ester, preferably 1 mol per 50 to 10,000 mols of ester, and most preferably 1 mol per 50 to 2,000 mols of ester.

The carbon monoxide is preferably employed in substantially pure form, as available commercially, but inert diluents such as carbon dioxide, nitrogen, methane, and noble gases can be present if desired. The presence of inert diluents does not affect the carbonylation reaction but their presence makes it necessary to increase the total pressure in order to maintain the desired CO partial pressure. The carbon monoxide, like the other reactants, should, however, be essentially dry, i.e., the CO and the other reactants should be reasonably free from water. The presence of minor amounts of water such as may be found in the commercial forms of the reactants is, however, acceptable. Hydrogen, which may be present in very small (trace) amounts as an impurity, is not objectionable and even may tend to stabilize the catalyst.

It has been previously found that the activity of the Group VIII noble metal catalysts described above can be significantly improved, particularly with respect to reaction rate and product concentration, by the concurrent use of a promoter. Effective promoters include the elements having atomic weights greater than 5 of Groups IA, IIA, IIIA, IVB, VIB, the non-noble metals of Group VIII and the metals of the lanthanide and actinide groups of the Periodic Table. Particularly preferred are the lower atomic weight metals of each of these groups, e.g. those having atomic weights lower than 100, and especially preferred are metals of Groups IA, IIA and IIIA as are metals of Group VIB and the non-noble metals of Group VIII. In general, the most suitable elements are lithium, magnesium, calcium, titanium, chromium, iron, nickel and aluminum. The particularly preferred elements are lithium and chromium. The promoters may be used in their elemental form, e.g. as finely-divided or powdered metals, or they may be employed as compounds of various types, both organic and inorganic, which are effective to introduce the element into the reaction system. Thus, typical compounds of the promoter elements include oxides, hydroxides, halides, e.g. bromides and iodides, oxyhalides, hydrides, alkoxides, and the like. Especially preferred organic compounds are the salts of organic mono-carboxylic acids, e.g. alkanoates such as acetates, butyrates, decanoates and laurates, benzoates, and the like. Other compounds include the metal alkyls, carbonyl compounds as well as chelates, association compounds and enol salts. Particularly preferred are the elemental forms, compounds whch are bromides or iodides, and organic salts, e.g. salts of the mono-carboxylic acid corresponding to the anhydride being produced. Mixtures of promoters can be used, if desired, especially mixtures of elements from different Groups of the Periodic Table. The exact mechanism of the effect of the promoter, or the exact form in which the promoter acts, is not known but it has been noted that when the promoter is added in elemental form, e.g. as a finely-divided metal, a slight induction period is observed.

The quantity of promoter can vary widely but preferably it is used in the amount of 0.0001 mol to 100 mols per mol of Group VIII noble metal catalyst, most preferably 0.001 to 10 mols per mol of catalyst.

In the working up of the reaction mixtures, e.g. by distillation, as discussed above, the promoter generally remains with the Group VIII metal catalyst, i.e. as one of the least volatile components, and is suitably recycled or otherwise handled along with the catalyst.

The activity of the Group VIII noble metal catalysts described above is also significantly improved, particularly with respect to reaction rate and product concentration, catalyst stability and corrosion inhibition, by the use of an organic promoter, and particularly advantageous is the concurrent use of a promoter combination or co-promoter system containing a metal component which is a metal of Groups IVB, VB and VIB, and the non-noble metals of Group VIII, in any of the forms described above, in association or combination with an organo-nitrogen compound or an organo-phosphorus compound wherein the nitrogen and the phosphorus are trivalent.

The organic promoter can, in its broader sense, be any organo-nitrogen or organo-phosphorus compound wherein the nitrogen and phosphorus are trivalent. Preferably, however, the organo-nitrogen promoter is an amine, especially a tertiary amine of the formula

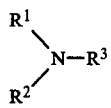

wherein $R^1$, $R^2$ and $R^3$ are the same or different and are alkyl, cycloalkyl, aryl or acyl groups which may be substituted by non-interfering groups, preferably having up to 20 carbon atoms, such as trimethylamine, triethylamine, triphenylamine, ethylenediamine tetraacetic acid, and the like, or a heterocyclic amine such as pyridine, picoline, quinoline, methylquinoline, hydroxy quinoline, pyrrole, pyrrolidine, pyrrolidone, and the like, or an imidazole, such as imidazole, methyl imidazole and the like, or an imide of a carboxylic acid which may be monobasic or polybasic and which may be aliphatic or aromatic and preferably contains up to 20 carbon atoms, such as acetic acid, succinic acid, phthalic acid, pyromellitic acid, e.g., N,N-dimethylacetamide, succinimide, phthalimide and pyromellitic diimide, or a nitrile or amide which may be aliphatic or aromatic and preferably contain up to 20 carbon atoms, e.g., acetonitrile, hexamethyl phosphoric triamide, and like imides, nitriles, and amides, or an oxime such as cyclohexanone oxime, and the like. It will be understood, however, that higher molecular weight promoters, e.g. polymeric forms of the organo-nitrogen compounds, may be used such as polyvinylpyridine, polyvinyl pyrrolidone, and the like.

The organo-phosphorus promoter is preferably a phosphine of the formula

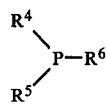

wherein $R^4$, $R^5$ and $R^6$ may be the same or different and are alkyl, cycloalkyl, aryl groups, amide groups or halogen atoms, preferably containing 1 to 20 carbon atoms in the case of alkyl and cycloalkyl groups and 6 to 18 carbon atoms in the case of aryl groups. Typical phosphines include trimethylphosphine, tripropylphosphine, tributyl phosphine, tricyclohexyphosphine and triphenylphosphine.

Although, preferably the organic promoters are added separately to the catalyst system, it is possible to add them as complexes with the Group VIII noble metal such as the trichloro trispyridine rhodium, tris(triphenyl phosphine) rhodium, chlorotris(triphenyl phosphine) rhodium, and chlorocarbonyl bis(triphenyl phosphine) rhodium, and like complexes. Both free organic promoters and complexed promoters can also be used. Indeed, when a complex of the organic promoter and the Group VIII noble metal is used, it is desirable to add free organic promoter as well. The amount of organic promoter will generally lie in the ranges referred to above for the metal promoter except that preferably up to 50 mols per mol of catalyst are employed.

The ratio of ester to the halide in the reaction system can vary over a wide range. Typically, there are used 1 to 500 equivalent of ester, preferably 1 to 200 equivalents per equivalent. Thus, there are typically used 1 to 500 mols, preferably 1 to 200 mols of ester per mol of halide reactant. By maintaining the partial pressure of carbon monoxide at the values specified, adequate amounts of the reactant are always present to react with the hydrocarbyl ester.

The carbonylation step is readily carried out in a single reaction zone to which a halide source, e.g., a hydrocarbyl halide such as methyl iodide, and the methyl acetate are both charged and are heated together, preferably in the liquid phase, in the presence of carbon monoxide and in the presence of the Group VIII metal catalyst. It will be understood that the hydrocarbyl halide may be formed in situ and the halide may thus be supplied to the system not only as the hydrocarbyl halide but the halogen moiety may also be supplied as another organic halide or as the hydro-halide or other inorganic halide, e.g. salts, such as the alkali metal or other metal salts, or even as elemental iodine or bromine.

As previously mentioned, in carrying out the carbonylation steps described above, a wide range of temperatures, e.g. 20° to 500° C. are suitable but temperatures of 100° to 300° C. are preferably employed and the more preferred temperatures generally lie in the range of 125° to 250° C. Temperatures lower than those mentioned can be used but they tend to lead to reduced reaction rates, and higher temperatures may also be employed but there is no particular advantage in their use. The time of reaction is also not a parameter of the process and depends largely upon the temperature employed, but typical residence times, by way of example, will generally fall in the range of 0.1 to 20 hours. The reaction is carried out under super-atmospheric pressure but excessively high pressures, which require special high-pressure equipment, are not necessary. In general, the reaction is effectively carried out by employing a carbon monoxide partial pressure which is preferably 5 to 2,000 psi, although carbon monoxide partial pressures of 0.1 to 15,000 psi can also be employed. The total pressure is that required to provide the desired CO partial pressure and preferably that required to maintain the liquid phase. Typically, total pressures up to about 3,000 psig are used but most preferably they are at most about 1,000 psig. The reaction can be advantageously carried out in an autoclave or similar apparatus.

As previously mentioned, it has been discovered that even though hydrogen is present in the carbonylation zone, even in large amounts, deactivation of the Group VIII noble metal catalyst, particularly in the case of a rhodium or palladium catalyst will occur unless a minimum partial pressure of hydrogen or 10 psi in accordance with the invention is supplied during the separation of volatile products from the Group VIII noble metal catalyst. Thus, the process of this invention is not only applicable to the carbonylation of esters to produce alkanoic anhydride, e.g., acetic anhydride by the carbonylation of methyl acetate, but it is also applicable to the regeneration of the Group VIII noble metal catalyst, especially a rhodium or palladium catalysts, employed for the preparation, in addition to the acetic anhydride, of ethylidene diacetate, acetaldehyde and acetic acid, as described in the above-mentioned Belgian Pat. No. 839,321 which is the counter-part of U.S. application Ser. No. 654,662 filed Feb. 5, 1976. Such carbonylation of methyl acetate is carried out as described above except that significant amounts of hydrogen are included with the carbon monoxide. The partial pressure of hydrogen employed falls within the above specified ranges for carbon monoxide partial pressure. Molar ratios of carbon monoxide to hydrogen, broadly within the range of 1:100 to 100:1, desirably within the range of 50:1 to 1:50, and preferably within the range of 10:1 to 1:10 can be employed. Molar ratios of carbon monoxide to hydrogen within the range of 0.1:5 to 5:1 are especially preferred. The molar ratios of carbon monoxide to hydrogen also affect the nature of the coproducts obtained. For example, other conditions remaining constant in a liquid phase system, increasing the molar ratio of carbon monoxide to hydrogen increases the molar ratio of acetic anhydride to acetic acid produced. Conversely, reducing the molar ratio of carbon monoxide to hydrogen increases the molar ratio of acetaldehyde to acetic acid produced.

It will be apparent that the carbonylations referred to above are carried out under substantially anhydrous conditions. The presence of minor amounts of water, however, such as may be found in commercially available reactants, is permissible. Normally, however, the presence of more than 5 mol % of water in any one or more of the reactants should be avoided, the presence of less than 3 mol % of water desired, and the presence of less than 1 mol % is preferred.

As previously mentioned, a carbon monoxide partial pressure of at least about 15 psi is advantageously maintained in the separation zone when the catalyst employed contains a metal promoter in addition to the Group VIII noble metal. It has been found that many of the metal promoters referred to above may tend to become insoluble in the reaction medium, particularly when used in relatively large amounts, and it has been discovered that the presence of the carbon monoxide tends to convert the metal promoter to a soluble form so that it is retained in solution. This is particularly true in the case of chromium and like metal promoters. In the case of metal promoters which already exist in a fully soluble form, the use of the carbon monoxide is not absolutely necessary but it is advisable to maintain the at least 15 psi partial pressure of carbon monoxide whenever a metal promoter is present. The presence of the carbon monoxide does not have any known bearing upon the effect of the at least 10 psi of hydrogen partial pressure in maintaining the activity of the Group VIII noble metal catalyst.

It has also been observed that the use of a hydrogen partial pressure of at least 10 psi during separation of volatile components from the catalyst in accordance with this invention makes it unnecessary to supply hydrogen to the carbonylation reaction and this makes it possible to achieve maximum selectivity to the anhydride, e.g., acetic anhydride when the anhydride is the desired product.

Ordinarily, partial pressures of hydrogen during separation greater than about 200 psi serve no useful purpose and it is generally undesirable to employ hydrogen partial pressures greater than about 250 psi. The same considerations apply to the partial pressures of carbon monoxide during volatile component separation. It is a particularly surprising feature of the invention that catalyst activity can be so effectively maintained with hydrogen partial pressures at the minimum 10 psi or only slightly higher in the separation zone, and that the correspondingly low partial pressures of carbon monoxide effectively maintain metal promoters in active form.

The following examples of specific application will serve to provide a fuller understanding of the invention but it will be understood that these examples are given for illustrative purposes only, however, and are not to be interpreted as limitative of the invention. In the examples, all parts are by weight unless otherwise indicated.

EXAMPLE I

Using a reactor in the form of a 1-gallon stirred autoclave provided with an inlet for liquid feed, and a line connected to a source of carbon monoxide, methyl acetate is carbonylated in the presence of a catalyst composed of rhodium trichloride trihydrate, tributyl phosphine and chromium hexacarbonyl, as follows. The reactor is charged with approximately 1.8 liters of a mixture of 20 parts of methyl iodide and 80 parts of methyl acetate containing approximately 0.03 mol (expressed as Rh) of rhodium trichloride trihydrate, 0.49 mol of tributyl phosphine and 0.03 mol (expressed as Cr) chromium hexacarbonyl, and then heated for one hour at 160° C. under a partial pressure of carbon monoxide of approximately 300 psi. Continuous operation is then begun with a feed of 300 g./hr. of methyl iodide and 1,200 g./hr. of methyl acetate. Carbon monoxide is supplied to the reactor at this time to maintain a continuous carbon monoxide partial pressure of about 400 psi (total pressure 550 psig). The liquid reaction mixture is continuously withdrawn from the reactor at the rate of 3,500 g./hr. and passes to a flash distillation chamber maintained under a pressure of 75 psig and a temperature of 125°–130° C. A partial pressure of 13 psi of hydrogen and 19 psi of carbon monoxide is maintained in the flash distillation, chamber in which approximately 1500 g./hr. of the liquid feed is volatilized, and about 2,000 gm. per hour of non-volatilized liquid containing the catalyst components is recycled to the reactor. Under these conditions it is found that methyl acetate is converted to acetic anhydride with a selectivity of 98%, and at the same time it is found that the rate of acetic anhydride formation is 0.874 mol/hr.-liter. After 125 hours of continuous operation, some of the catalyst is withdrawn from the recycle stream so that the catalyst concentration in the reactor is reduced about 50%. The rate of acetic anhydride formation then becomes 0.625 mol/hr-liter and continues at this rate, the catalyst maintaining full activity throughout this period. Then the partial pressure of hydrogen in the flash chamber is reduced to zero for 36 hours and during this time the activity of the catalyst is found to drop significantly so that the rate of acetic anhydride formation is found to fall from the uniform 0.625 mol/hr-liter previously observed to only 0.15 mol/hr.-liter and continues to fall. At this point, hydrogen is again introduced into the flash chamber to provide a partial pressure of hydrogen of 15 psi (the partial pressure of carbon monoxide remaining at about 20 psi). Immediately the rate of acetic anhydride formation begins to increase and after about 25 hours becomes stabilized at the rate observed at the same catalyst concentrations before the hydrogen partial pressure was eliminated.

EXAMPLE II

Using a reactor in the form of a 1-gallon stirred autoclave provided with an inlet for liquid feed, a line connected to a source of hydrogen, and a line connected to a source of carbon monoxide, methyl acetate is carbonylated in the presence of a catalyst composed of rhodium trichloride trihydrate, tributyl phosphine and chromium hexacarbonyl, as follows. The reactor is charged with approximately 1.8 liters of a mixture of 25 parts of methyl iodide and 75 parts of methyl acetate containing approximately 0.03 mol (expressed as Rh) of rhodium trichloride trihydrate, 0.49 mol of tributyl phosphine and 0.03 mol (expressed as Cr) chromium hexacarbonyl, and then heated for one hour at 160° C. under a partial pressure of carbon monoxide of approximately 250 psi and a hydrogen partial pressure of approximately 150 psi. Continuous operation is then begun with a feed of 150 g./hr. of methyl iodide and 475 g./hr. of methyl acetate. Carbon monoxide is supplied to the reactor at this time to maintain a continuous carbon monoxide partial pressure of about 250 psi and a continuous hydrogen partial pressure of 150 psi (total pressure 500 psig). The liquid reaction mixture is continuously withdrawn from the reactor at the rate of 2,900 g./hr. and passes to a flash distillation chamber maintained under a pressure of 55 psig and a temperature of 115°–120° C. A partial pressure of 19 psi of hydrogen and 22 psi of carbon monoxide are maintained in the flash distillation chamber in which approximately 650 g./hr. of the liquid feed is volatilized and about 2250 gm. per hour of non-volatilized liquid containing the catalyst components is recycled to the reactor. Under these conditions it is found that methyl acetate is converted to acetic anhydride with a selectivity of 82%, and at the same time it is found that the rate of acetic anhydride formation is 0.561 mol/hr.-liter. The presence of hydrogen in the reactor leads to the concurrent formation of products resulting from the action of carbon monoxide and hydrogen upon methyl acetate such as ethylidene diacetate and acetaldehyde. During 40 hours of operation the activity of the catalyst is constant viz. catalyst maintaining full activity throughout this period. When the partial pressure of hydrogen in the flash chamber is reduced to zero but all other operations continued, the activity of the catalyst is found to drop significantly so that the rate of acetic anhydride formation is found to fall from the uniform rate previously observed to an extent corresponding to the decrease noted in Example I. Similarly, when hydrogen is again introduced into the flash chamber to provide a partial pressure of hydrogen of 19 psi (the partial pressure of carbon monoxide remaining at about 22 psi), immediately the rate of acetic anhydride formation begins to increase and, as in Example I, becomes stabilized at the rate observed before the hydrogen partial pressure was eliminated.

EXAMPLE III

Again using a reactor in the form of a 1-gallon stirred autoclave provided with an inlet for liquid feed, a line connected to a source of hydrogen and a line connected to a source of carbon monoxide, methyl acetate is carbonylated in the presence of a catalyst composed of rhodium trichloride trihydrate and tributyl phosphine, as follows. The reactor is charged with approximately 1.8 liters of a mixture of 25 parts of methyl iodide and 75 parts of methyl acetate containing approximately 0.03 mol (expressed as Rh) of rhodium trichloride trihydrate, and approximately 0.25 mol of tributyl phosphine and then heated for one hour at 160° C. under a partial pressure of carbon monoxide of approximately 220 psi and a partial pressure of hydrogen of about 130 psi. Continuous operation is then begun with a feed of 160 g./hr. of methyl iodide and 500 g./hr. of methyl acetate. Carbon monoxide and hydrogen are supplied to the reactor at this time to maintain a continuous carbon monoxide partial pressure of about 220 psi and a continuous hydrogen partial pressure of about 130 psi (total pressure 500 psig). The liquid reaction mixture is continuously withdrawn from the reactor at the rate of 1,100 g./hr. and passes to a flash distillation chamber maintained under a pressure of 55 psig and a temperature of 110°–115° C. A partial pressure of 16 psi of hydrogen and 24 psi of carbon monoxide are maintained in the flash distillation chamber in which approximately 660 g./hr. of the liquid feed is volatilized and about 440 g. per hour of non-volatilized liquid containing the catalyst components is recycled to the reactor. Under these conditions it is found that methyl acetate is converted to acetic anhydride with a selectivity of 66%, and at the same time it is found that the rate of acetic anhydride formation is 0.362 mol/hr.-liter. The presence of hydrogen in the reactor leads to the concurrent formation of products resulting from the action of carbon monoxide and hydrogen upon methyl acetate such as ethylidene diacetate and acetaldehyde. During 56 hours of operation the activity of the catalyst is constant viz, catalyst maintaining full activity throughout this period. When the partial pressure of hydrogen in the flash chamber is reduced to zero but all other operation continued, the activity of the catalyst is found to drop significantly the rate of acetic anhydride formation is found to decrease as observed in Examples I and II. When, however, hydrogen is again introduced into the flash chamber to provide a partial pressure of hydrogen of 16 psi (the partial pressure of carbon monoxide remaining at about 24 psi), immediately the rate of acetic anhydride formation begins to increase and, as in Examples I and II, becomes stabilized at the rate observed before the hydrogen partial pressure was eliminated. On the other hand, when the CO partial pressure in the separation zone is reduced to zero, no change in catalyst activity is observed as long as the hydrogren partial pressure is maintained.

What is claimed is:

1. In the carbonylation of alkyl esters in the presence of a Group VIII noble metal catalyst wherein there is produced a reaction product comprising volatile components and the non-volatile Group VIII noble metal catalyst, and the volatile components are separated from said catalyst, the improvement which comprises providing a hydrogen partial pressure of at least 10 psi during the separation of the volatile products in the zone in which said separation is effected.

2. A process as defined in claim 1, wherein the Group VIII noble metal catalyst includes a metal promoter and a partial pressure of at least 15 psi of carbon monoxide is also applied.

3. A process as defined in claim 1, wherein the alkyl ester is methyl acetate and the Group VIII noble metal catalyst comprises rhodium and/or palladium.

4. A process as defined in claim 1, wherein the hydrogen partial pressure is in the range of 10 to 250 psi.

5. A process as defined in claim 2, wherein the carbon monoxide partial pressure is in the range of 15 to 250 psi.

* * * * *

UNITED STATES PATENT AND TRADEMARK OFFICE
CERTIFICATE OF CORRECTION

PATENT NO. : 4,252,741
DATED : February 24, 1981
INVENTOR(S) : Richard V. Porcelli, et al.

It is certified that error appears in the above-identified patent and that said Letters Patent are hereby corrected as shown below:

Col. 1, line 5 - "of anhydrides" should be --of the anhydrides--

Col. 1, line 6 - "acid" should be --acids--

Col. 1, line 26 - "low" should be --lower--

Col. 1, line 65 - "exaple" should be --example--

Col. 2, line 1 - "Pat. No." should be --patent--

Col. 3, line 49 - in the bracket, "Gl" should be --Cl--

Col. 7, line 2 - "or" should be --of--

Signed and Sealed this

Twenty-fifth Day of May 1982

[SEAL]

Attest:

Attesting Officer

GERALD J. MOSSINGHOFF

Commissioner of Patents and Trademarks